United States Patent
Meythaler et al.

(10) Patent No.: US 6,682,508 B1
(45) Date of Patent: Jan. 27, 2004

(54) DIRECT CENTRAL NERVOUS SYSTEM CATHETER AND TEMPERATURE CONTROL SYSTEM

(75) Inventors: Jay M. Meythaler, Birmingham, AL (US); Jean Peduzzi, Clanton, AL (US); Landon C. Miller, Tuscalosa, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/914,801

(22) PCT Filed: Mar. 3, 2000

(86) PCT No.: PCT/US00/05740

§ 371 (c)(1),
(2), (4) Date: Dec. 3, 2001

(87) PCT Pub. No.: WO00/51669

PCT Pub. Date: Sep. 8, 2000

Related U.S. Application Data

(60) Provisional application No. 60/148,055, filed on Aug. 10, 1999, and provisional application No. 60/122,642, filed on Mar. 3, 1999.

(51) Int. Cl.[7] .......... A61M 5/00; A61M 25/16; A61M 25/18; A61M 31/00; A61M 25/00; A61F 7/12; A61F 7/00; A61B 5/02; A61B 5/00; A61N 1/08; A61N 1/10; A61N 1/18; A61N 1/20; A61N 1/32; A61N 1/34; A61N 1/40

(52) U.S. Cl. .......... 604/246; 604/66; 604/113; 604/284; 604/537; 600/485; 600/561; 607/62; 607/96

(58) Field of Search .......... 604/43, 48, 803, 604/505, 508, 65–67, 93.01, 113–114, 151, 246–249, 256, 257, 264, 268, 523, 533, 534–535, 537, 284, 890.1; 607/62, 96–99; 137/340; 606/27–31; 600/549, 561, 573, 581, 485

(56) References Cited

U.S. PATENT DOCUMENTS

| | | | | |
|---|---|---|---|---|
| 4,613,324 A | | 9/1986 | Ghajar | 604/49 |
| 4,621,647 A | * | 11/1986 | Loveland | 600/561 |
| 4,655,745 A | | 4/1987 | Corbett | 604/49 |
| 4,723,556 A | | 2/1988 | Sussman | 128/748 |
| 4,784,638 A | | 11/1988 | Ghajar et al. | 604/49 |
| 4,904,237 A | * | 2/1990 | Janese | 604/28 |
| 4,950,232 A | | 8/1990 | Ruzicka et al. | 604/43 |
| 5,360,397 A | * | 11/1994 | Pinchuk | 604/27 |
| 5,364,377 A | * | 11/1994 | O'Neil | 156/294 |
| 5,474,547 A | | 12/1995 | Aebisher et al. | 604/891.1 |
| 5,531,673 A | | 7/1996 | Helenowski | 604/9 |
| 5,569,267 A | | 10/1996 | Howard, III et al. | 606/130 |

(List continued on next page.)

*Primary Examiner*—Brian L. Casler
*Assistant Examiner*—Catherine Serke
(74) *Attorney, Agent, or Firm*—Gifford, Krass, Groh, Sprinkle, Anderson & Citkowski, P.C.

(57) ABSTRACT

A central nervous system (CNS) catheter assembly (20) adapted for use as a ventriculostomy catheter and a spinal catheter includes a catheter body (28) defining at least one lumen (30) therethrough having a drug delivery branch (22) and a monitoring/sensing branch (24). The drug delivery branch (22) and the monitoring/sensing second branch (24) are in fluid communication with the lumen (30). The assembly further includes a filter assembly (36) disposed in fluid communication with the drug delivery branch (22) and a valve assembly (54) disposed in fluid communication with the monitoring/sensing branch (24). Also in accordance with the present invention, there is provided a temperature control system (170) for use in controlling the temperature of a location within the central nervous system such as the brain or the spinal cord. The system further includes a pump controller (180), a central processing unit or controller (194), a temperature sensing element (184), and a power supply (194) all operatively connected to the temperature control mechanism.

26 Claims, 4 Drawing Sheets

U.S. PATENT DOCUMENTS

| | | | |
|---|---|---|---|
| 5,772,625 A | 6/1998 | Krueger et al. | 604/9 |
| 5,832,932 A | 11/1998 | Elsberry et al. | 128/898 |
| 5,846,220 A | 12/1998 | Elsberry | 604/49 |
| 5,897,528 A | 4/1999 | Schultz | 604/49 |
| 5,957,912 A | 9/1999 | Heitzmann | 604/533 |
| 5,964,705 A | 10/1999 | Truwit et al. | 600/423 |
| 6,026,316 A | 2/2000 | Kucharczyk et al. | 600/420 |
| 6,061,587 A | 5/2000 | Kucharczyk et al. | 600/411 |

* cited by examiner

DIRECT CENTRAL NERVOUS SYSTEM CATHETER AND TEMPERATURE CONTROL SYSTEM

This application claims benefit of Prov. Appl. No. 60/122,642 filed Mar. 3, 1999 and Prov. Appl. No. 60/148,055 filed Aug. 10, 1999.

FIELD OF THE INVENTION

The subject invention relates to a catheter assembly and, more specifically, to a direct central nervous system catheter assembly suitable for use for: the simultaneous measurement of intracranial pressure, draining of cerebrospinal fluid (CSF), delivery of therapeutic agents and/or drug(s) directly into the cerebrospinal fluid, and a temperature control system which can be coupled to the direct central nervous system catheter to prevent or reduce damage to the central nervous system.

BACKGROUND OF THE INVENTION

By way of background, ventriculostomy catheters are commonly used to facilitate the drainage of cerebrospinal fluid (CSF) to reduce intracerebral pressure and can also be connected to pressure transducers for the monitoring of intracranial pressure (ICP). The increased use of ventriculostomy catheters can be directly associated with the publication of Guidelines to the Management of Severe Head Injury (Bullock et al. (1995) Guidelines for the Management of Severe Head Injury. San Francisco: Brain Trauma Foundation, Inc.; Rosner et al. (1992) *J. Neurosurgery* 76:399A; Rosner et al. (1990) *J. Trauma* 30:933–41; Rosner (1987) "Cerebral perfusion pressure: The link between intracranial pressure and systemic circulation". In Wood (ed.): Cerebral Flood Flow: Physiologic and Clinical Aspects. McGraw Hill, New York, N.Y., pp. 425–88, 1987). These Guidelines recommend the use of either a pressure bolt against the cerebral membranes or that a ventriculostomy be performed to directly measure ICP in all patients with a head injury and a Glascow coma score (GCS) of less than 10. Additionally, ventriculostomies are often utilized because of the added feature of allowing direct access to the CSF at the level of the brain. This is of particular importance as these catheters allow direct access to the CSF, which allows for direct withdrawal of CSF to control increased intracranial pressure, monitor drug levels or metabolites in the CSF (Kossman et al. (1996) *J. Antimicrob. Chemother.* 37(1):161–7), or to remove toxic substances from the CSF flow (Kristofet al. (1998) *J. Neurol. Neurosurg. Psychiatry.* 64(3):379–81).

Current ventriculostomy catheters are generally "open systems" of the single lumen-type, and as stated above, are typically linked to pressure transducers to give measurements of ICP, and are used to facilitate the drainage of CSF to reduce intracerebral pressure by disconnecting the pressure monitor and extracting. CSF fluid, and then reconnecting the pressure monitor. This creates the potential for the introduction of infectious agents which can cause infections such as ventriculitis or meningitis. As such, one of the most significant concerns of intracranial pressure monitoring is the potential introduction of pathogens into the CNS resulting in ventriculitis, meningitis and cerebral abscesses (Rossi et al. (1998) *Acta Neurochir. Suppl.* 71:91–3; Khan et al. (1998) *Acta Neurochir. Suppl.* 71:50–2; Guyot et al. (1998) *Acta Neurochir. Suppl.* 71:47–9; Holloway et al. (1996) *J. Neurosurg.* 85(3):419–24). The current ventriculostomy catheters are not designed, nor was it ever envisioned, that they would be used for drug delivery directly into the CSF. Furthermore, they are not generally approved for this use although some instances have been reported where they have been used for the delivery of antibiotics into the CSF. However, use of current ventriculostomy catheters in this manner remains a "non-approved use."

Similar to the present day ventriculostomy catheters, spinal catheters having an external port have been utilized for many years for the sampling of CSF and for the delivery of medications to the CSF in and around the spinal cord. These medications include anesthetics and acute pain medications. In animal models of induced CNS injury it has been suggested that intrathecal or intraventricular delivery may be of use to attenuate the amount of injury (Buki et al. (1999) *J. Neurotrauma* 16(6):511–21).

While the current ventriculostomy catheters and spinal catheters have been utilized for the introduction of drugs or medications therethrough, the current types of these catheters are not specifically designed for the delivery of drugs therethrough and, hence, impart drawbacks, the most critical of which includes the opportunity for and the introduction of infectious agents directly into the cerebral spinal fluid causing, for example, ventriculitis and/or meningitis.

It is known that in order to prevent or reduce injury or damage to elements of the central nervous system, such as the brain or spinal cord, that artificial conditions can be induced in the central nervous system such as the induction of a coma to slow the metabolism of the brain to keep its tissues viable. One such method for accomplishing this end is disclosed in U.S. Pat. No. 5,149,321 to Klatz et al. in which chilled drug containing fluids are delivered to the brain through catheters inserted in blood vessels such as the carotid artery. However, the prior art does not teach a method for directly maintaining or controlling the temperature of the CSF to aid in the treatment of central nervous system injuries.

Temperature has been linked to the degree of injury in CNS trauma induced in animals (Clark et al. (1996) *J. Cereb. Blood Flow Metab.* 16(2):253–61; Whalen et al. (1997) *J. Neurotrauma* 14(8):561–72). In essence, if the temperature can be lowered there will be a reduction in the area and amount of neuronal damage (Dietrich (1992) *J. Neurotrauma* 9 Suppl. 2:S475–85; Dietrich et al. (1996) *Adv. Neurol.* 71:177–94, discussion 194–7; Palmer et al. (1993) *J. Neurotrauma* 10(4):363–72). It has recently been theorized that a local reduction in the area of injury is required to reduce the amount and extent of induced injury to the brain while avoiding the complications associated with whole body cooling (Dietrich et al. (1996) *Adv. Neurol.* 71:177–94, discussion 194–7). It is likely that these same principles apply to spinal cord injury.

Accordingly, it would be both advantageous and desirable to have a catheter design which allows both direct access to the central nervous system (CNS) (e.g., the cerebral spinal fluid disposed about the brain and/or spinal cord) which would facilitate the measurement of ICP, the removal of CSF under aseptic circumstances, the aseptic introduction of therapeutic agents and/or drugs directly into the cerebral spinal fluid, and which can be combined with a temperature control system to control the temperature of the CSF to prevent or reduce damage to the central nervous system and to facilitate treatment of an individual in need of such treatment.

SUMMARY OF THE INVENTION

In accordance with the present invention, there is provided a direct central nervous system catheter which can be directly inserted into the ventricle space or spinal canal to provide access which enables the sampling of the CSF and/or monitoring of intracranial pressure while at the same time facilitating the aseptic delivery of therapeutic agents and/or drugs directly into the cerebrospinal fluid and the management of CSF temperature. The direct CNS catheter includes a catheter body defining at least one lumen and having a drug delivery branch, a monitoring/sensing branch, and optional branches if desired each branch being connected in fluid communication with the lumen. Both the drug delivery branch and the monitoring branch have at least one proximally disposed opening which provides for the introduction and/or removal of fluid therefrom. The drug delivery branch of the catheter assembly includes a filter connected in fluid communication therewith to remove any pathogens from a therapeutic agent and/or drug(s) delivered to the cerebrospinal fluid through the branch. The catheter assembly can also include a one-way valve for the introduction of drugs, fluids or medications through the catheter assembly with no back-flow of the introduced materials. With this design, the catheter assembly limits the introduction of pathogens into the system and reduces the potential contact of the health care provider to bodily fluids. Finally, the catheter assembly reduces the risk of losing an introduced therapeutic agent due to back-flow. The drug delivery branch is disposed distally to a sampling branch which allows for the withdrawal of fluids. The monitoring branch allows for direct measurement of CSF pressure using monitoring or sensing equipment. This includes monitoring pressure waves of the cerebrospinal fluid through the end of the catheter placed in the ventricle or spinal canal of a brain. The catheter assembly can also include a control valve disposed in fluid communication with an optional branch which includes an in-line one-way valve that allows the direct sampling of the cerebrospinal fluid for either laboratory testing or to lower intracranial pressure in a sterile fashion. The monitoring branch is connected in fluid communication with the catheter body through a second control valve. The monitoring branch allows for pressure monitoring or sensing and the control valve allows for the measurement of intracranial pressure in a first position wherein an open fluid pathway is established between the portion of the catheter disposed in the ventricle or spinal canal and the monitoring branch and wherein fluid communication between the portion of the catheter in the ventricle or spinal canal and the fluid sampling branch is closed. The control valve is movable to a second position wherein fluid communication between the portion of the catheter inserted in the ventricle or spinal canal and the sampling branch is opened whereby fluid can be extracted from the patient. In the second portion, fluid communication between the pressure monitoring branch and the portion of the catheter disposed in the ventricle or spinal canal is closed.

The catheter assembly provides a "closed system" which means that the system is not open to the atmosphere. Once the catheter is constructed from its modular connections, there is no reason to open the closed system for either drug delivery, pressure monitoring, temperature management, or CSF sampling and withdrawal.

Also in accordance with the present invention, there is provided a temperature control system for use in controlling the temperature of a location within the central nervous system such as the brain or the spinal cord. The temperature control system includes a temperature control mechanism including a pump operatively connected in fluid communication to a heat exchanger. The heat exchanger includes a closed-loop conduit system connected in fluid communication with the heat exchanger which can be placed within and/or adjacent to a portion of the central nervous system of a patient through, for example, insertion in an optional branch of the direct central nervous system catheter which has been placed in contact with a portion of a subject's central nervous system. The system further includes a pump controller, a central processing unit or controller, and a power supply all operatively connected to the temperature control mechanism.

BRIEF DESCRIPTION OF THE DRAWINGS

The following detailed description is best understood with reference to the following drawings in which.

DETAILED DESCRIPTION OF THE INVENTION

Figure 1:
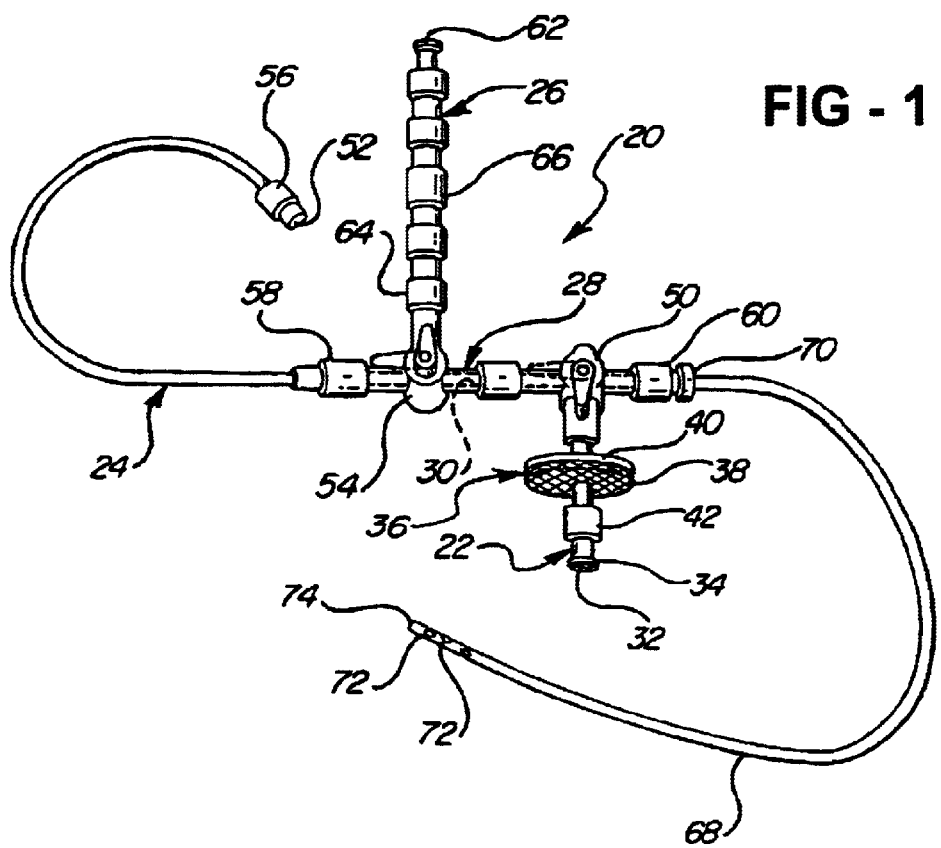
FIG. 1 is a perspective view of an embodiment of the catheter assembly of the present invention.

Referring to FIG. 1, a central nervous system (CNS) catheter assembly is generally shown at 20. The assembly 20 is to be inserted via an insertion device such as a wire disposed inside the catheter assembly 20 into either the spinal canal or ventricles of the brain in order to remove cerebrospinal fluid (CSF), monitor intracranial pressure (ICP), and/or deliver therapeutic agents and/or drugs intrathecally and/or intraventricularly, directly into the cerebrospinial fluid.

The CNS catheter assembly 20 includes branches 22,24, 26 and a main body 28 which defines at least one lumen 30 therethrough. The branches 22,24,26 and main catheter body 28 are preferably tubular in shape.

The branch 22 includes a proximally disposed opening or port 32 which provides access to the lumen 30. The branch 22 is preferably designed for the introduction or delivery of drugs therethrough. The branch 22 can also include a connector or adapter 34 disposed directly adjacent to or about the proximal opening or port 32 which allows for the connection or attachment of a fluid delivery device, such as a syringe, to the branch 22 for delivery of a therapeutic agent and/or a drug therethrough. The connector 34 can be any suitable connector such as a modular-type connector, a quick-release or Luer-type connector, a cap having, for example, a reclosable diaphragm to allow repeated needle puncturing, or other screw down-type connectors, all of which are well known to those skilled in the art.

The branch 22 further includes a micro-filter assembly 36 which is disposed in-line and in fluid communication with the branch 22. The filter assembly 36 allows for the aseptic introduction of drugs into the cerebrospinal fluid of a patient without the potential for delivery of harmful microorganisms into the cerebrospinal fluid which can cause CNS infections including ventriculitis or meningitis. Preferably, the filter assembly 36 includes a membrane-type or micropore filter 38 disposed substantially perpendicular with respect to the lumen 30 and fluid flow path. That is, the filter 38 lies transversely across or substantially perpendicular to the lumen 30. The filter assembly 36 can also include a support 40 which provides support to the filter 38 during the delivery of the drug therethrough to enable the filter 38 to withstand pressures applied by the fluid delivery device. The filter 38 can include any suitable filter media which can include any suitable hydrophobic or hydrophilic material such as cellulose fiber, polysulfones, polyamides, polyolefins, polyesters, and fluoropolymers. This list of materials is not intended to be exhaustive and other suitable materials can be utilized without departing from the present invention.

Figure 2:
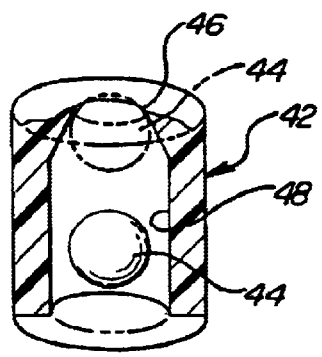
FIG. 2 is an enlarged perspective view of a valve assembly for the present invention.

The branch 22 can also include a one-way valve 42 disposed in between the filter assembly 36 and the connector 34 which prevents back-flow of fluid into the catheter assembly 20 and/or the ventricle space or spinal canal. Referring to FIG. 2, the valve. 42 is preferably a one-way valve or other suitable type or design including a ball valve or any other type or design known to those skilled in the art which remains in a closed position to drug delivery (shown in phantom) wherein the ball 44 seals an opening 46, until the pressure exerted on the ball 44 by the drug delivery forces the ball 44 to move to an open position 44' wherein the ball 44 is clear of the opening 46 to allow the drug to flow into the filter assembly 36. The valve 42, as shown in FIG. 2, is activated by the back pressure from the CSF or any other cause. In this valve assembly, back pressure from the CSF or any other cause maintains a ball 44 disposed in a conduit 48 in a first position (shown in phantom) directly adjacent to and in contact with the opening 46 to prevent flow through the valve assembly 42. Then, upon the application of pressure from the delivery of a drug or the like through the valve assembly 42, the ball 44 would be displaced to a second position (as shown) away from the opening 46 whereby the flow path through the conduit 48 allows the movement of fluid, i.e., drugs, to pass through the valve assembly 42 and ultimately into the patient.

The branch 22 is disposed in fluid communication with the main body 28 and can include a multi-position control valve 50 disposed therebetween to, in a first position (shown in phantom), allow the introduction of a drug through the branch 22 while preventing any drug from flowing in the proximal direction, and, in a second position (as shown), allow for pressure monitoring and/or fluid extraction while closing the drug delivery pathway.

The branch 24 can be used as an ICP monitoring/sensing branch which includes a proximally disposed opening or port 52 which can be attached to a pressure transducer in order to monitor ICP or other parameters and/or to allow the removal of CSF. The pressure monitoring branch 24 can also be connected to a multi-position control valve 54 disposed in fluid communication therewith. The control valve 54 is preferably a multi-position valve which prevents the flow of fluid distally away from the opening or port 52 and also maintains a constant pressure so that the pressure monitoring branch 24 of the catheter assembly 20 is not compromised by fluid flowing in the reverse direction. The valve 54 is movable between a first position (as shown) wherein the monitoring branch 24 is in fluid communication with the main body 28 and the portion of the catheter assembly 20 disposed in the ventricle or spinal canal to allow ICP monitoring and a second position (shown in phantom) wherein ICP monitoring through the monitoring branch 24 is interrupted or closed and fluid communication between the third/sampling branch 26 and the main body 28 and the portion of the catheter disposed in the ventricle or spinal canal is established. The valve assemblies 50,54 can be any suitable valve known to those skilled in the art such as a standard ball-cock valve or stop-cock valve. The valves 50,54 are preferably three-way valves having a first position, a second position, and a third position.

The branch 24 can also include a connector 56 similar to that of connector 34 described above disposed adjacent to the opening or port 52 to facilitate the use of the branch 24 with various devices including a pressure transducer and/or syringe and/or needle.

Additionally, at least one connector 58, similar in style to the connector 34 and preferably without the reclosable diaphragm, can be disposed in-line as shown in FIG. 1. A further optional connector 60 similar to the connector 34 but preferably without a diaphragm can be disposed in-line in the catheter body 28 as shown in FIG. 1.

The sampling branch 26 is disposed in fluid communication with the main body 28. The multi-position control valve 54 is disposed between the branch 26 and the main body 28. The sampling branch 26 includes an opening or port 62 disposed at its distal end. A connector 64 similar to those discussed above can also be disposed at the distal end of the branch 26. The sampling branch 26 can also include a one-way valve 66 disposed between the port 62 and the valve 54 similar to the valve 42 described above. The valve 66 is oriented in the opposite direction to the valve 42 to allow fluid withdrawal or extraction.

At the distal end of the catheter body 28, an intraventricular or spinal canal catheter portion 68 is affixed. The intraventricular or spinal canal catheter portion 68 is the portion of the catheter assembly 20 inserted into the ventricle space or the spinal canal. The intraventricular or spinal canal portion 68 can be permanently affixed to the catheter body 28 or it can be connected through a connector 70 to the connector 60 such as following placement of the intraventricular or spinal canal catheter portion 68 within a patient. The intraventricular or spinal canal catheter portion 68 can include at least one port 72 disposed substantially adjacent to an end or distal tip 74 of the main body 28 of the catheter assembly 20. The end 74 may or may not be closed. In a preferred embodiment, shown in FIG. 1, several ports 72 are helically disposed on the intraventricular or spinal canal catheter portion 68. Each port 72 can be formed by using a low power laser to ablate material to form the port 72. In operation, the end 74 of the catheter assembly 20 is inserted into either the intraventricular space or the spinal canal in order to place the port 72 in contact with the CSF. The end 74 can also include a diaphragm which can remain closed or, when pierced, will remain open. That is, the diaphragm is not self-sealing.

Figure 3:
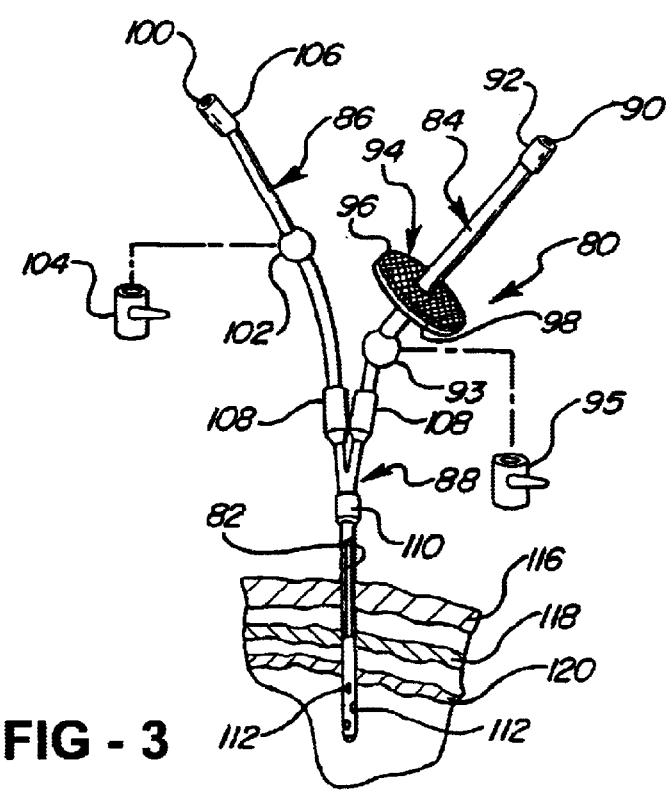
FIG. 3 is a schematic diagram illustrating an alternative embodiment of the CNS catheter of the present invention.

Referring to FIG. 3, an alternative embodiment of the central nervous system (CNS) catheter assembly is generally shown at 80. The assembly 80 is to be inserted into either the spinal canal or ventricles of the brain in order to remove cerebrospinal fluid (CSP) via an insertion device such as a wire disposed inside a lumen 82, to monitor intracranial pressure (ICP), and/or deliver drugs, such as intrathecally, directly into the cerebrospinal fluid.

The CNS catheter assembly 80 includes a pair of branches 84,86 and a main body 88 which defines at least one lumen 82 therethrough. Both the branches 84,86 and main body 88 are preferably oriented in an essentially "Y" shaped orientation.

Figure 4:
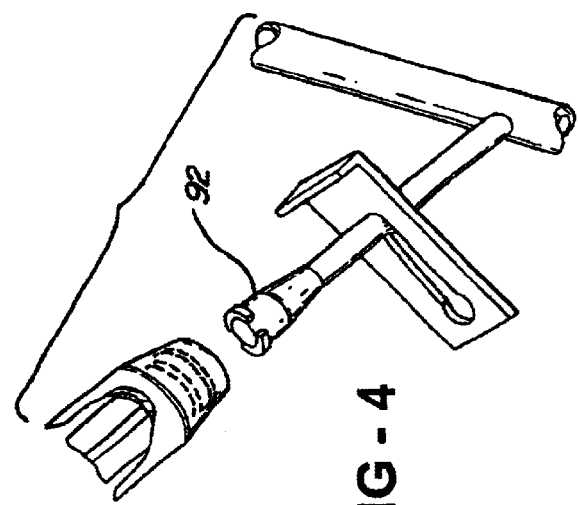
FIG. 4 is an enlarged view of a connector used in cooperation with the catheter assembly of the present invention.

The branch 84 includes a proximally disposed opening 90 which provides access to the lumen 82. The branch 84 is preferably designed for the introduction or delivery of drugs therethrough. The branch 84 can also include a connector or adapter 92 disposed directly adjacent to or about the proximal opening or port 90 which allows for the connection or attachment of a fluid delivery device, such as a syringe, to the branch 84 for delivery of a drug therethrough. The connector 92 can be any suitable connector such as a quick-release or Luer-type connector capable of attaching a syringe thereto, for example (see FIG. 4), a cap having a reclosable diaphragm to allow repeated needle puncturing, or other screw down-type connectors known to those skilled in the art. It may also be a one-way valve similar to the valve 42 described above.

The branch 84 can also include a valve assembly 93 which is preferably a one-way valve similar to those described above but can also be any suitable valve known to those skilled in the art such as a standard ball-cock valve or stop-cock valve 95.

The branch 84 further includes a micro-filter assembly 94 which is disposed in-line and in fluid communication with the branch 84. The filter assembly 94 allows for the aseptic introduction of drugs into the cerebrospinal fluid of a patient without the potential for delivery of harmful microorganisms into the cerebrospinal fluid. Preferably, the filter assembly 94 includes a membrane-type or micro-pore filter 96 disposed substantially perpendicular with respect to the lumen 82 and fluid flow path. That is, the filter 96 lies transversely across the lumen 82. The filter 96 can also include a support 98 which provides support to the filter 96 during the delivery of the drug therethrough to enable the filter 96 to withstand pressures applied by the fluid delivery device.

Figure 5:
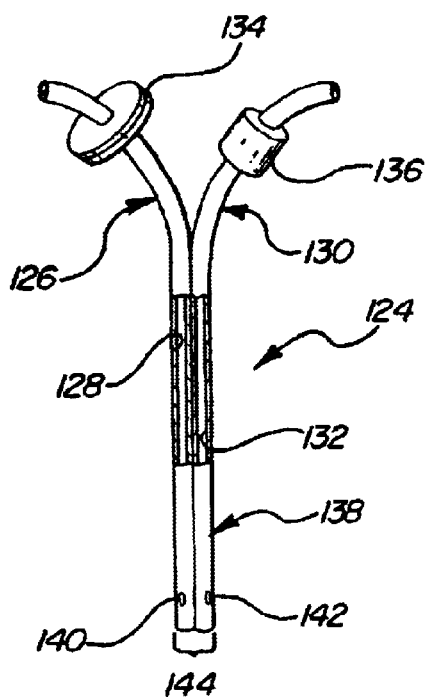
FIG. 5 is a schematic diagram illustrating an alternative embodiment of the CNS catheter of the present invention.

Referring to FIG. 5, a further alternative embodiment of the catheter assembly of the present invention is generally shown at 124. The catheter assembly 124 includes a first branch. 126 which defines a first fluid lumen 128 therethrough and a second branch 130 which defines a second fluid lumen 60 therethrough. As already described above for the embodiment shown in FIG. 3, the first branch 126 is designed for the delivery of drugs into the CSF and includes a fluid filtering assembly 134. The second branch 130 which is designed for the monitoring of ICP and/or removal of CSF also includes a valve assembly 136 as described above.

In this embodiment, the first branch 126 and the second branch 130 each define their own lumen 128,132, respectively. The catheter assembly 124 has the same "Y" shape as the embodiment illustrated in FIG. 3; however, the first 126 and second 130 branches come together to define a main body 138 but maintain separate and distinct fluid carrying lumens 128,132. The lumen 128 includes at least one port 140 disposed therein for allowing the introduction or delivery of a drug into the CSF. The lumen 132 includes at least one port 142 which allows for the monitoring and/or removal of CSF from a patient. As described for the embodiment shown in FIG. 3, the catheter assembly 124 includes a proximally disposed end 144 wherein ends of each lumen 128,132 may be open or closed, respectively, depending on design choice.

Figure 6:
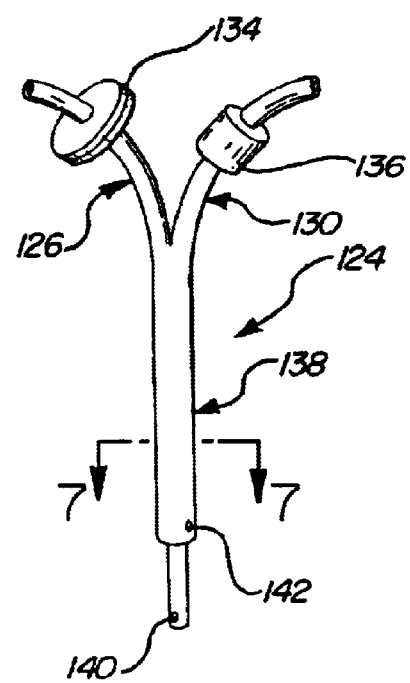
FIG. 6 is a schematic diagram illustrating a further alternative embodiment of the CNS catheter of the present invention.
Figure 7:
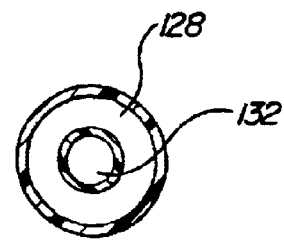
FIG. 7 is a cross-sectional view of a portion of the CNS catheter of the present invention taken along line 7—7 of FIG. 6.

Referring now to FIG. 6, a further alternative embodiment is illustrated wherein like numerals indicate like or corresponding parts throughout the several views. In this embodiment, rather than having the lumens 128,132 of branches 126,130 diverge into their separate respective lumens 128,132 disposed adjacent to one another, the lumens 128,132 are concentrically disposed with respect to one another as best shown in FIG. 7. That is, the first branch 126 and the second branch 130 remain separated from one another at the proximal end of the catheter assembly 124 while in the main body portion 138 of the catheter assembly 124, the branches 126,130 and their respective lumens 128,132 become concentrically disposed with respect to one another. As was the case for the embodiment illustrated in FIG. 5, each lumen 128,132 can include at least one port 140,142, respectively.

The branches 22,24,26,84,86,126,130 of the catheter assemblies 20,80,124 can be manufactured of any suitable material. Preferably the branches 22,24,26,84,86,126,130 are constructed of a plastic material such as silicone plastic.

The mainbody 28,88,138 is preferably made of a plastic material such as a silicone rubber compound for use as an intraventricular catheter and silicone plastic for use as an intrathecally.

All of the connectors or adapters are preferably industry norm standard connectors such as mating-type connectors or adapters, such as the Luer-lock type, or threaded connectors or adapters which reduce the likelihood that the connectors made therewith will inadvertently come apart potentially exposing the closed system to contamination.

Figure 8:
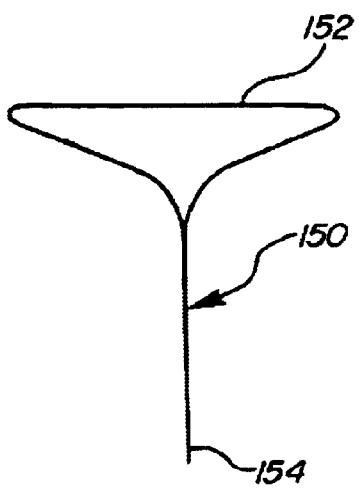
FIG. 8 is a front view of an insertion device for use with the present invention.
Figure 9:
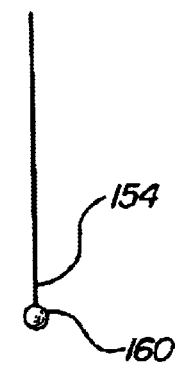
FIG. 9 is an enlarged view of an embodiment of the insertion apparatus.
Figure 10:
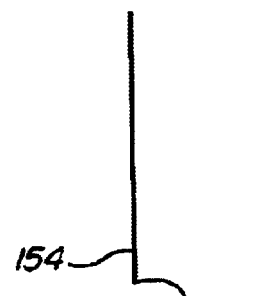
FIG. 10 is an alternative embodiment of the insertion apparatus.

Referring to FIGS. 8, 9 and 10, several embodiments of the wire insertion device are shown. FIGS. 8 and 10 show an insertion device 150 having a triangularly-shaped handle portion 152. The insertion device 150 includes a distal end 154 which is initially inserted into the lumen of the catheter assembly. As shown in FIG. 9, a ball 160 can be disposed as the distal end 154 of the insertion device 150. The ball 160 is of a specific size and shape such that it allows for the insertion of the insertion device 150 into the lumen of the catheter assembly without piercing the end 74,144 of the main body 28,88,138 disposed in the patient.

Referring to FIG. 10, an alternative distal end configuration for the wire insertion device 150 is shown which includes a sharp point or cutting surface 162 disposed at its distal end 154 which is capable of piercing a closed end 74,144 or diaphragm of the main body 28,88,138 upon insertion and proper placement of the assembly 20,80,124.

Figure 12:
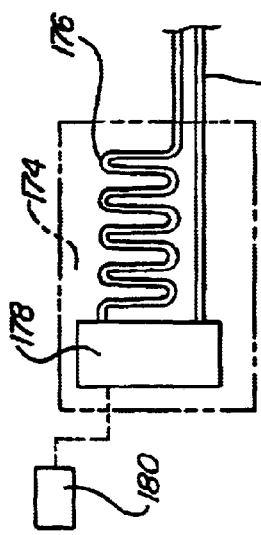
FIG. 12 is a schematic of a heat exchanger system operative in the present invention.
Figure 11:
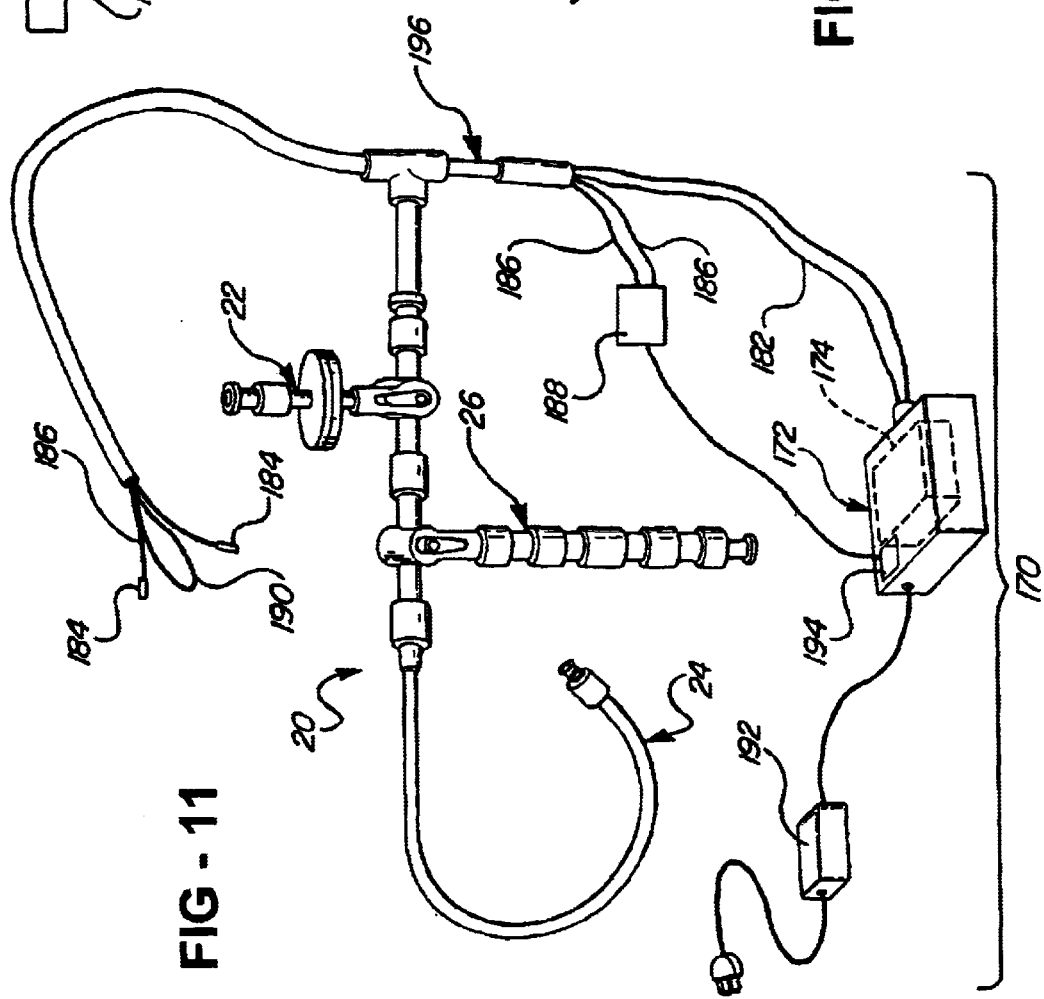
FIG. 11 is a schematic illustration of the temperature control system of the present invention coupled with a catheter of the present invention.

Referring to FIG. 11, a further embodiment of the present invention is shown. A temperature control system is generally shown at 170. The system 170 includes a temperature control mechanism 172 operatively connected to a direct central nervous system catheter 20 which is similar to the catheter assembly described above and as described hereinbelow. The temperature control mechanism 172 includes a reservoir 174 disposed therein for receiving and retaining a temperature conducting fluid or thermal transfer fluid such as ethylene glycol, water or normal saline or other suitable materials such as polyethylene glycol therein. Referring to FIG. 12, a heat exchanger 176 is disposed within the reservoir 174 in contact with the thermal transfer fluid disposed in the reservoir 174. A pump 178 operatively connected to a pump controller 180 serves to move the thermal transfer fluid through the heat exchanger 176. A thermostatically controlled heating/cooling mechanism, disposed within the reservoir 174 selectively heats or cools the thermal transfer fluid disposed in contact therewith. The thermal transfer fluid contacts the heat exchanger 176 and thereby regulates the temperature of the thermal transfer fluid being circulated or pumped to the CNS location. A conduit 182 is connected in fluid communication with the heat exchanger 174 to form a closed loop system. The conduit 182 is connected in fluid communication with the heat exchanger 174 and serves to transport the thermal transfer fluid from the heat exchanger 174 into the central nervous system of a subject in order to directly control the local temperature of the central nervous system of the subject through contact with either the CSF or CNS tissue itself.

The temperature control system 170 can also include a temperature sensor or element 184 which is connected in electrical communication via line 186 to a temperature computation device 188 which is connected to the control mechanism 172. The temperature sensor or element 184 can be a thermistor or similar device which converts temperature measurement into an electrical signal which is converted to a temperature readout by the temperature computation device 188. The temperature sensor or element 184 is disposed in contact with or directly adjacent to the central nervous system fluid (CSF) or tissue of the subject in general proximity to or adjacent to a closed end 190 of the conduit 182 in order to ascertain temperature measurements of the central nervous system in the general vicinity of the closed end 190 of the conduit 182.

The temperature control mechanism 172 can be powered by a power supply 192 which provides a predefined source of current to the temperature control device 172 in order for its operation.

The temperature control mechanism 172 can also include a controller or central processing unit (CPU) 194 which provides overall control to the temperature maintenance and to the operation of the temperature control mechanism 172. Additionally, a pump controller 180 can be connected in electrical communication with the pump 178 to further aid in the control of the rate of flow and the temperature management of the thermal transfer fluid.

Referring again specifically to FIG. 11, the temperature control system 170 preferably is combined with a direct central nervous system catheter assembly 20,88,124, as described in detail above, which includes a first branch 22,84,126, a second branch 24,86,130, or an optional third branch 26 operatively connected to a main body 28,88,138 which defines at least one lumen therein.

Unique to the embodiment shown in FIG. 11, the catheter assembly 20 includes a fourth branch 196 in which the closed loop end 190 of the temperature control device 172 is inserted in order to be placed within or adjacent to the central nervous system and/or central nervous system fluid (i.e. CSF). The temperature sensor or element 184 can also be inserted through the branch 196 in order to be placed in contact with the central nervous system and/or adjacent to the closed end 190 of the conduit 182 of the temperature control mechanism 172.

In operation, the direct central nervous system catheter assembly 20 would be disposed within either the intraventricular space or the spinal canal of a subject in order to place the end 74,144 of the portion of the catheter body inserted into the patient either in contact with or adjacent to the cerebrospinial fluid. The closed loop end 190 of the conduit 182 would be disposed within the lumen defined by the branch into which the closed end 190 is inserted and would be moved through the main body 28,88,138 of the catheter assembly 20,80,124 into contact with the cerebrospinal fluid. The temperature sensor or element 184 could also be placed within the intraventricular space or spinal canal concurrently with the placement of the closed end 190 of the conduit 182 or optionally could be placed either before or after the placement of the closed end 190 of the conduit 182. Following proper positioning of the closed end 190 of the conduit 182, thermal transfer fluid having a desired temperature can be pumped through the conduit 182 where it would flow to the closed end 190 and via the heat transfer capacity of the conduit material and/or thermal transfer fluid, either heat or cool the central nervous system fluid. The thermal transfer fluid would then return to the temperature control device 172 via the conduit 182 where it would be recycled through the heat exchanger 176 and recirculated back to the closed end 190 of the conduit 182 for further control of the temperature at the desired CNS site. The flow rate and temperature of the thermal transfer fluid can be adjusted to regulate the temperature.

The conduit 182 is preferably made of a material which has suitable heat transfer characteristics embodied by various types of plastic tubing.

The catheter assembly 20,80,124 of the present invention provides a system that allows for the monitoring of ICP, sampling of CSF, drug delivery, and/or temperature regulation of the CSF of a patient or subject without opening the catheter system to the environment after the catheter assembly has been placed. That is, once the catheter assembly of the present invention is inserted into a patient, all of the immediately recited functions can be accomplished by connecting the appropriate device to the appropriate branch and manipulating the proper valves accordingly. Thus, all of the functions can be accomplished aseptically without directly exposing the CNS to the external atmosphere where pathogens could be present.

Figure 13:
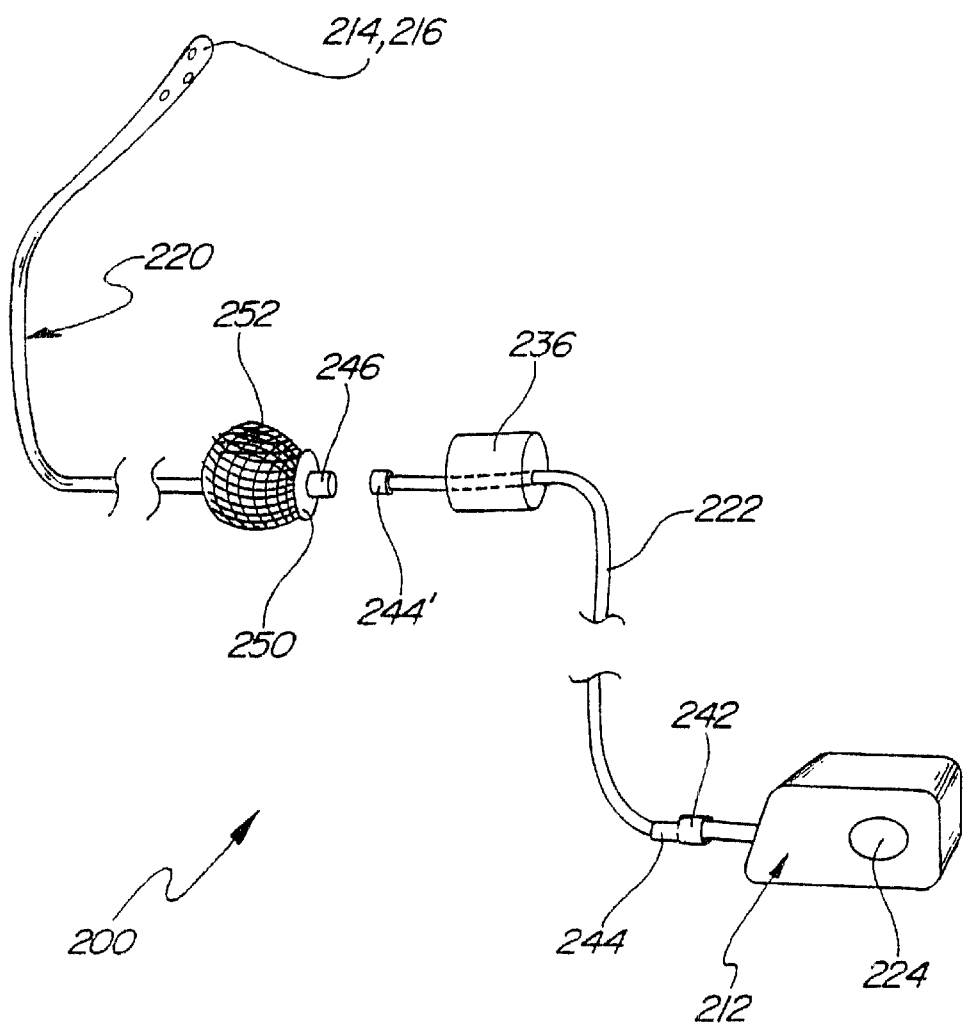
FIG. 13 is a schematic diagram illustrating a further alternative embodiment of the CNS catheter of the present invention.

Referring now to FIG. 13, a further alternative embodiment is illustrated of the central nervous system (CNS) catheter assembly generally at 200. The assembly 200 has an external pump 212 that permits the delivery of a variety of drugs and vectors in a sterile manner to the intraventricular end 214 or, alternatively, the intrathecal end 216 of a catheter 220 are connected to a replaceable intermediate catheter branch 222. The external pump 212 is a disposable low cost pump. Preferably, the pump 212 is battery powered and more preferably has a refillable pump chamber 224. The pump 212 is connected to the intermediate branch catheter 222 by a valve 242. The valve 242 is preferably a one-way valve or other suitable type or design including a ball valve, or one-way needle insertion valve, or any other type or design known to those skilled in the art which remains in a closed position to drug delivery until the pressure exerted on the valve by the drug delivery forces the valve to an open position. A complementary one-way valve fitting 244 connects the valve 242 of pump 212. Preferably, the complementary one-way valve fitting 244 is a male needle head one-way valve. The branch 222 further includes a microfilter assembly 236 which is disposed in line and in fluid communication with the branch 222. The filter assembly 236 allows for the aseptic introduction of drugs or vectors through the assembly 200 without the potential for delivery of harmful microorganisms therewith. The microfilter assembly 236 corresponds to the microfilter assembly 36 described with respect to FIG. 1. Branch 222 terminates in a one-way valve head 244' similar to one-way valve fitting 244. Preferably, the one-way valve fitting 244' is a male needle head one-way valve. One-way valve fitting 244' is adapted to engage a complementary valve 246 of the catheter 220. Preferably, the one-way valve 246 is a one-way needle insertion valve similar to that detailed with respect to valve 242. As catheter 220 is implanted, the one-way valve 246 is backed by a coverlet 250 serving as a physical barrier to infection and thereby permitting repeated antibiotic applications. Preferably, the coverlet 250 is adhered to the dermal layer about the catheter 220 with a surgical adhesive. Preferably, to facilitate structural adherence of the replaceable intermediate catheter within the patient body, a mesh 252 surrounds the portion of the catheter 220 that traverses the dermal layer. The mesh 252 is attached to the catheter tube 220 and the coverlet 250. The mesh 252 serves to allow skin to interpenetrate the mesh 252 and thereby stabilize the implanted catheter assembly. The mesh 252 is formed of any surgically implantable mesh material conventional to the art illustratively including stainless steel, titanium, fluoropolymer, polyamides and biologically surface modified forms thereof. The catheter 220 is in fluid communication with an intraventricular end 214 or intrathecal end 216 of the catheter according to the present invention. Thus, the external pump catheter assembly 200 according to the present invention is able to deliver a variety of drugs and vectors for times extending up to and beyond six months in a sterile and controlled manner. The external pump 212 is readily disconnected temporarily for service or aseptic refilling of the pump chamber 224.

In view of the teaching presented herein, other modifications and variations of the present inventions will be readily apparent to those of skill in the art. The foregoing drawings, discussion, and description are illustrative of some embodiments of the present invention, but are not meant to be limitations on the practice thereof. It is the following claims, including all equivalents, which define the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed is:

1. A central nervous system (CNS) catheter assembly adapted for use as a ventriculostomy catheter and a spinal catheter, said CNS catheter assembly comprising:
    a catheter body defining at least one lumen therethrough having at least a first branch and a second branch, said first branch and said second branch in fluid communication with said at least one lumen, said catheter body further comprising an insertable portion for insertion within a ventricle space or spinal canal of a subject, said first branch at a first distance relative to said insertable portion that is equal to or less than a second distance between said second branch and said insertable portion;
    an opening in fluid communication with said at least one lumen disposed at a proximal end of said first branch;
    an opening in fluid communication with said at least one lumen disposed at a proximal end of said second branch;
    at least one opening in fluid communication with said at least one lumen disposed at a distal end of said catheter body;
    an aseptic drug delivery filter assembly disposed in fluid communication with said first branch; and
    a first valve disposed in fluid communication with said second branch wherein the valve is positioned to allow fluid communication between the lumen of the second branch and the lumen of the catheter body without disrupting fluid communication between the lumen of the first branch and the lumen of the catheter body.

2. A catheter assembly according to claim 1, wherein said first branch includes at least one valve disposed in fluid communication therewith.

3. A catheter assembly according to claim 2, wherein said valve comprises a one-way flow valve.

4. By A catheter assembly according to claim 1, wherein said filter assembly includes a micro-pore filter.

5. A catheter assembly according to claim 1, wherein said filter assembly includes a membrane filter.

6. A catheter assembly according to claim 1, wherein said catheter body comprises a single lumen.

7. A catheter assembly according to claim 1, wherein said first branch comprises a connector disposed at the proximal end thereof.

8. A catheter assembly according to claim 1, wherein said second branch comprises a connector disposed at the proximal end thereof.

9. A catheter assembly according to claim 1 further including a third branch disposed in fluid communication with said catheter body.

10. A catheter assembly according to claim 9 further including a second valve disposed in fluid communication with said catheter body and said third branch.

11. A catheter assembly according to claim 1, wherein said insertable portion is affixed to said catheter body.

12. A catheter assembly according to claim 1, wherein said insertable portion is removably affixed to said catheter body.

13. A catheter assembly according to claim 1 wherein said first branch and said second branch form a Y-shaped intersection with said at least one lumen.

14. A central nervous system temperature control system adapted for use with a central nervous system catheter assembly, said system comprising:
    a temperature control mechanism comprising a closed-loop heat exchanger operatively connected in fluid communication to a conduit which is placed in fluid communication with central nervous system fluid through a catheter assembly comprising a central nervous system (CNS) catheter assembly adapted for use as a ventriculostomy catheter and a spinal catheter, said CNS catheter assembly comprising:
        a catheter body defining at least one lumen therethrough having at least a first branch and a second branch, said first branch and said second branch in fluid communication with said at least one lumen, said catheter body further comprising an insertable portion for insertion within a ventricle space or spinal canal of a subject;
        an opening in fluid communication with said at least one lumen disposed at a proximal end of said first branch;
        an opening in fluid communication with said at least one lumen disposed at a proximal end of said second branch;
        at least one opening in fluid communication with said at least one lumen disposed at a distal end of said main body;

an aseptic drug delivery filter assembly disposed in fluid communication with said first branch; and a first valve disposed in fluid communication with said second branch.

15. A system according to claim 14, wherein the temperature control mechanism includes temperature sensing elements operatively connected to the temperature control mechanism.

16. A system according to claim 15, wherein the temperature sensing element comprises a thermistor.

17. A method for controlling the temperature of cerebrospinal fluid, said method comprising the steps of:

disposing a catheter in direct contact with the cerebrospinal fluid of a subject;

disposing a conduit within the catheter and in contact with the cerebrospinal fluid, the conduit connected in fluid communication to a temperature control device comprising a closed-loop heat exchanger;

measuring the temperature of the cerebrospinal fluid; and circulating fluid from the closed-loop heat exchange through the conduit while within the subject to control the temperature of the cerebrospinal fluid.

18. A method according to claim 17 further comprising the step of adjusting the temperature of the fluid circulating in the conduit.

19. A method according to claim 17 further comprising the step of adjusting the rate of flow of the fluid through the conduit.

20. A method for aseptic drug delivery to the central nervous system through a catheter and cerebrospinal fluid, and monitoring of intracranial pressure or intraspinal pressure, said method comprising the steps of:

inserting a catheter into either a ventricular space, a spinal canal, or both, comprising:

a catheter body defining at least one lumen therethrough having at least a first branch, a second branch, and a third branch, said first branch, said second branch, and said third branch in fluid communication with said at least one lumen, said catheter body having an insertable portion for insertion within a ventricle space or spinal canal of a subject; an opening in fluid communication with said at least one lumen disposed at a proximal end of said first branch; an opening in fluid communication with said at least one lumen disposed at a proximal end of said second branch; at least one opening in fluid communication with said at least one lumen disposed at a distal end of said main body; a filter assembly disposed in fluid communication with said first branch; a first valve movable between a first position wherein fluid can flow through the second branch and not the third branch and a second position wherein fluid cannot flow to the second branch and can flow to the third branch disposed in fluid communication with said second branch and the third branch; and a second valve movable between a first position wherein fluid can flow through the first branch and not the second branch and a second position wherein fluid cannot flow to the first branch and can flow to the second or the third branch;

delivering a drug through the first branch by positioning the second valve in the first position without opening the catheter to the atmosphere wherein the valve locations and the position of the branch relative to the other branches enables drug delivery without disrupting pressure regulation monitoring.

21. A method according to claim 20 further including the step of monitoring intracranial pressure or intraspinal pressure by connecting a pressure monitoring device to the second branch and positioning the first valve in the first position and the second valve in the second position.

22. A method according to claim 20 further including the step of removing cerebrospinal fluid through the third branch by positioning the second valve in the second position and the first valve in the second position without opening the catheter to the atmosphere.

23. A catheter assembly comprising a central nervous system (CNS) catheter assembly adapted for use as a ventriculostomy catheter and a spinal catheter, said CNS catheter assembly comprising:

a catheter body defining at least one lumen therethrough having at least a first branch sand a second branch, said first branch and said second branch in fluid communication with said at least one lumen, said catheter body further comprising an insertable portion for insertion within a ventricle space or spinal canal of a subject;

an opening in fluid communication with said at least one lumen disposed at a proximal end of said first branch;

an opening in fluid communication with said at least one lumen disposed at a proximal end of said second branch;

at least one opening in fluid communication with said at least one lumen disposed at a distal end of said main body;

an aseptic drug delivery filter assembly disposed in fluid communication with said first branch;

a first valve disposed in fluid communication with said second branch; and an external pump in fluid communication with said first branch.

24. A catheter assembly according to claim 23 wherein said external pump is battery powered.

25. A catheter assembly according to claim 23 wherein said external pump has a refittable pump chamber.

26. A method for aseptic drug delivery to the central nervous system through a catheter and cerebrospinal fluid, and monitoring of intracranial pressure or intraspinal pressure, said method comprising the steps of:

inserting a catheter into either a ventricular space, a spinal canal, or both, comprising:

a catheter body defining at least one lumen therethrough having at least a first branch, a second branch, and a third branch, said first branch, said second branch, and said third branch in fluid communication with said at least one lumen, said catheter body having an insertable portion for insertion within a ventricle space or spinal canal of a subject; an opening in fluid communication with said at least one lumen disposed at a proximal end of said first branch; an opening in fluid communication with said at least one lumen disposed at a proximal end of said second branch; at least one opening in fluid communication with said at least one lumen disposed at a distal end of said main body; a filter assembly disposed in fluid communication with said first branch; a first valve movable between a first position wherein fluid can flow through the second branch and not the third branch and a second position wherein fluid cannot flow to the second branch and can flow to the third branch disposed in fluid communication with said second branch and the third branch; and a second valve movable between a first position wherein fluid can flow through the first branch and not the second branch and a second position wherein fluid cannot flow to the first branch and can flow to the second or the third branch;

delivering a drugs through the first branch by positioning the second valve in the first position without opening the catheter to the atmosphere, wherein said drug is delivered from an external pump through the first branch.

* * * * *